United States Patent [19]

Yoon

[11] Patent Number: 5,779,680

[45] Date of Patent: Jul. 14, 1998

[54] RETRACTABLE SAFETY NEEDLE INSTRUMENT WITH MOVABLE SAFETY MEMBER

[76] Inventor: InBae Yoon, 2101 Highland Ridge Dr., Phoenix, Md. 21131

[21] Appl. No.: 371,687

[22] Filed: Jan. 13, 1995

Related U.S. Application Data

[63] Continuation-in-part of Ser. No. 247,205, May 20, 1994, Pat. No. 5,634,934, and Ser. No. 254,007, Jun. 3, 1994, Pat. No. 5,478,317, which is a division of Ser. No. 800,507, Nov. 27, 1991, abandoned, and a continuation of Ser. No. 800,507, Nov. 27, 1991, abandoned, Ser. No. 79,586, Jun. 22, 1993, Pat. No. 5,423,770, and Ser. No. 260,439, Jun. 15, 1994, Pat. No. 5,423,760, which is a division of Ser. No. 868,578, Apr. 15, 1992, Pat. No. 5,336,176, and Ser. No. 237,734, May 4, 1994, pending which is a continuation of Ser. No. 868,578, Apr. 15, 1992, Pat. No. 5,336,176.

[51] Int. Cl.$^6$ ............................................. A61M 5/178
[52] U.S. Cl. ........................... 604/164; 604/165; 604/158
[58] Field of Search ..................................... 604/157, 158, 604/164, 165, 167, 264, 274; 606/185

[56] References Cited

U.S. PATENT DOCUMENTS

| | | |
|---|---|---|
| Re. 32,922 | 5/1989 | Levin et al. . |
| 1,527,291 | 2/1925 | Zorraquin . |
| 2,496,111 | 1/1950 | Turkel . |
| 2,623,521 | 12/1952 | Shaw . |
| 2,630,803 | 3/1953 | Baran . |
| 4,254,762 | 3/1981 | Yoon . |
| 4,345,589 | 8/1982 | Hiltebrandt . |
| 4,442,836 | 4/1984 | Meinecke et al. . |
| 4,488,545 | 12/1984 | Shen . |
| 4,503,856 | 3/1985 | Cornell et al. . |
| 4,535,773 | 8/1985 | Yoon . |
| 4,559,041 | 12/1985 | Razi . |
| 4,601,710 | 7/1986 | Moll . |
| 4,627,841 | 12/1986 | Dorr . |
| 4,654,030 | 3/1987 | Moll et al. . |
| 4,670,008 | 6/1987 | Von Albertini . |
| 4,677,979 | 7/1987 | Burns . |
| 4,747,831 | 5/1988 | Kulli . |
| 4,802,275 | 2/1989 | Haber et al. . |
| 4,817,603 | 4/1989 | Turner et al. . |
| 4,869,717 | 9/1989 | Adair . |
| 4,889,117 | 12/1989 | Stevens . |
| 4,900,307 | 2/1990 | Kulli . |
| 4,902,280 | 2/1990 | Lander . |
| 4,906,236 | 3/1990 | Alberts et al. . |
| 4,931,042 | 6/1990 | Homes et al. ............... 606/185 X |
| 4,943,280 | 7/1990 | Lander . |
| 4,946,446 | 8/1990 | Vadher . |

(List continued on next page.)

FOREIGN PATENT DOCUMENTS

| | | |
|---|---|---|
| 2544262 | 4/1977 | Germany . |
| 1435246 | 11/1988 | Russian Federation . |

*Primary Examiner*—Sam Rimell

[57] ABSTRACT

A safety needle instrument for establishing a portal in the wall of an anatomical cavity includes a housing, a cannula either fixed to the housing or distally-biased and movable relative to the housing between an extended rest position and a proximally spaced retracted position, a needle disposed within the cannula and movable relative to the cannula between an extended position where a distal end of the needle protrudes distally from a distal end of the cannula and a retracted position proximally spaced from the extended position, a distally-biased safety shield disposed between the cannula and the needle and movable relative to the needle between an extended safety shield rest position protecting the needle distal end when the needle is retracted and a safety shield retracted position exposing the needle distal end when the needle is extended, a retracting mechanism for moving the needle from the needle extended position to the needle retracted position, a handle or knob for manually moving the needle from the needle retracted position to the needle extended position, a locking mechanism for locking the needle in the needle extended position, and a releasing mechanism responsive to penetration of the safety needle instrument into the anatomical cavity.

34 Claims, 9 Drawing Sheets

U.S. PATENT DOCUMENTS

| | | |
|---|---|---|
| 4,955,870 | 9/1990 | Ridderheim et al. . |
| 4,966,593 | 10/1990 | Lennox . |
| 4,973,316 | 11/1990 | Dysarz . |
| 4,994,042 | 2/1991 | Vadher . |
| 4,994,068 | 2/1991 | Hufnagle . |
| 5,024,665 | 6/1991 | Kaufman . |
| 5,026,388 | 6/1991 | Ingaiz . |
| 5,030,206 | 7/1991 | Lander . |
| 5,053,016 | 10/1991 | Lander . |
| 5,061,251 | 10/1991 | Juhasz . |
| 5,066,288 | 11/1991 | Deniega et al. . |
| 5,104,382 | 4/1992 | Brinkerhoff et al. . |
| 5,104,383 | 4/1992 | Shichman . |
| 5,114,407 | 5/1992 | Burbank . |
| 5,116,353 | 5/1992 | Green . |
| 5,127,909 | 7/1992 | Shichman . |
| 5,129,885 | 7/1992 | Green et al. . |
| 5,152,754 | 10/1992 | Plyley et al. . |
| 5,158,552 | 10/1992 | Borgia et al. . |
| 5,207,647 | 5/1993 | Phelps . |
| 5,217,451 | 6/1993 | Freitas .......................... 604/164 X |
| 5,226,426 | 7/1993 | Yoon . |
| 5,226,891 | 7/1993 | Bushatz et al. . |
| 5,290,243 | 3/1994 | Chodorow et al. . |
| 5,290,304 | 3/1994 | Storace . |
| 5,295,993 | 3/1994 | Green . |
| 5,312,354 | 5/1994 | Allen et al. . |
| 5,318,580 | 6/1994 | Gresl, Jr. . |
| 5,318,585 | 6/1994 | Guy et al. . |
| 5,320,610 | 6/1994 | Yoon . |
| 5,324,268 | 6/1994 | Yoon . |
| 5,330,432 | 7/1994 | Yoon . |
| 5,330,497 | 7/1994 | Freitas et al. ...................... 604/164 X |
| 5,336,176 | 8/1994 | Yoon . |
| 5,338,305 | 8/1994 | Plyley et al. . |
| 5,342,382 | 8/1994 | Brinkerhoff et al. . |
| 5,346,459 | 9/1994 | Allen . |
| 5,350,393 | 9/1994 | Yoon . |
| 5,360,405 | 11/1994 | Yoon . |
| 5,372,588 | 12/1994 | Farley et al. . |
| 5,376,082 | 12/1994 | Phelps . |
| 5,399,167 | 3/1995 | Deniega ................................ 604/164 |
| 5,423,796 | 6/1995 | Shikhman et al. .................. 604/167 X |
| 5,437,643 | 8/1995 | Transue .................................. 604/164 |
| 5,527,335 | 6/1996 | Bolduc et al. ...................... 604/164 X |

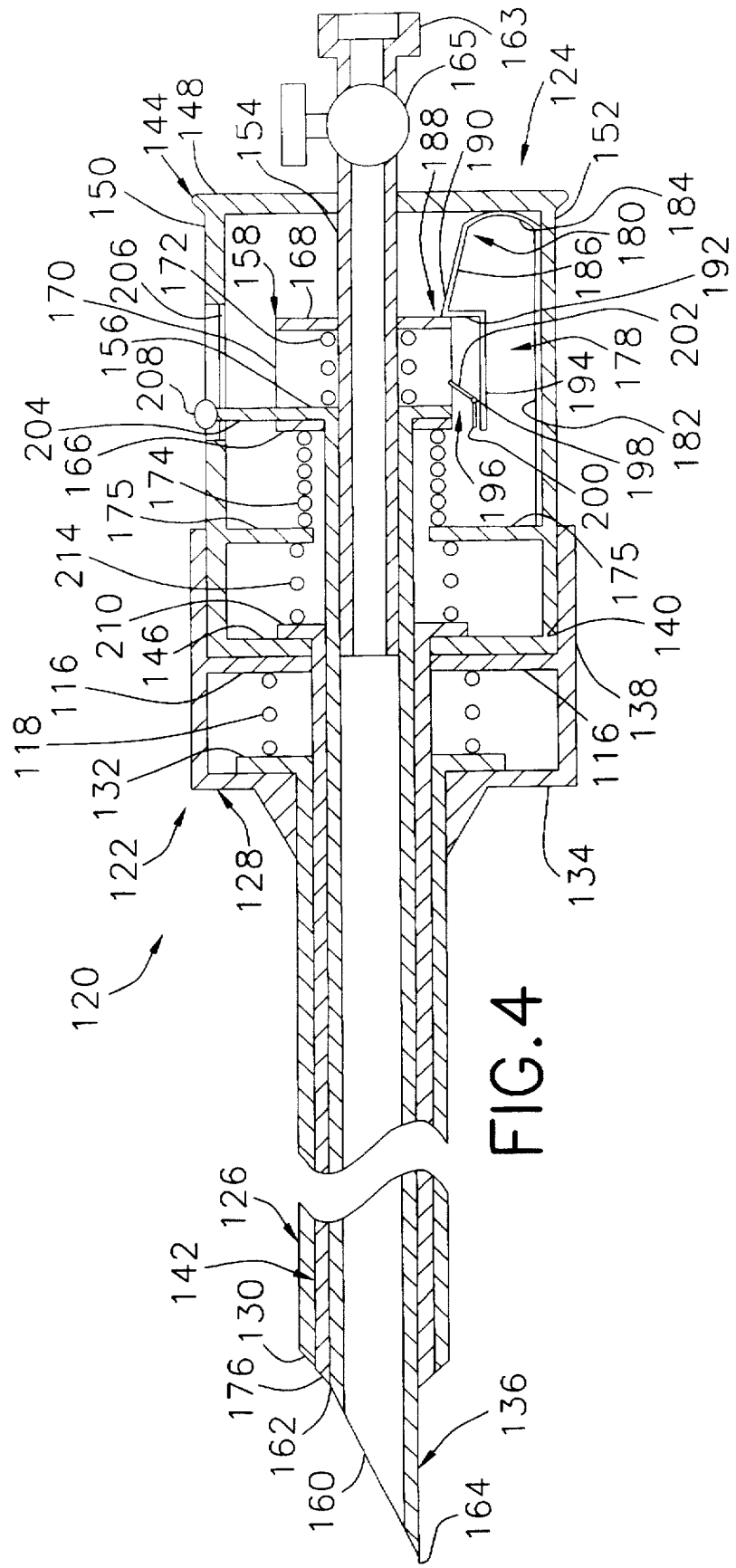

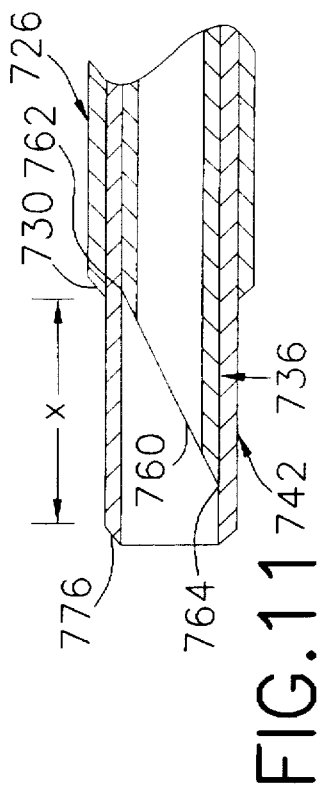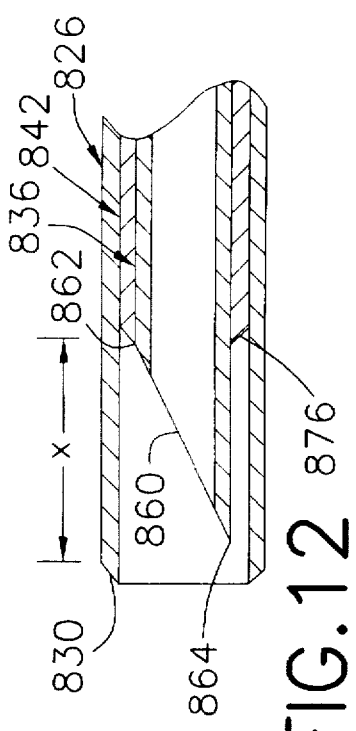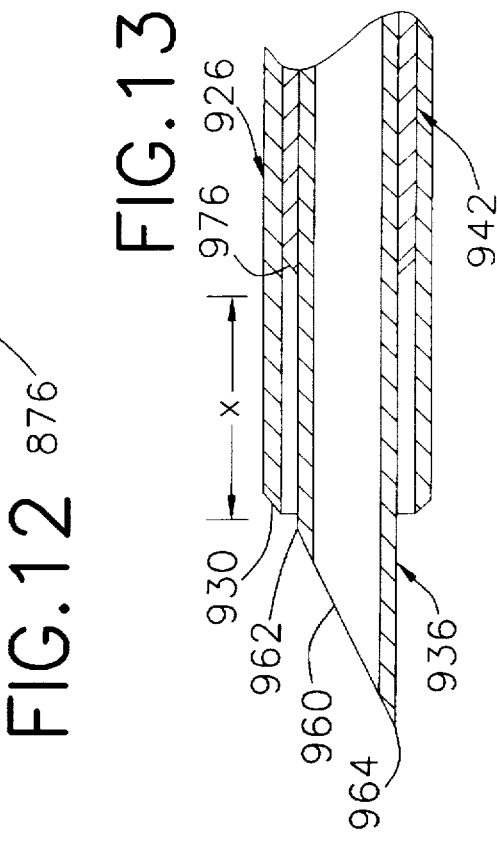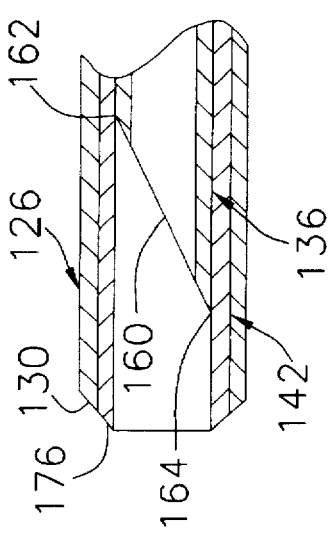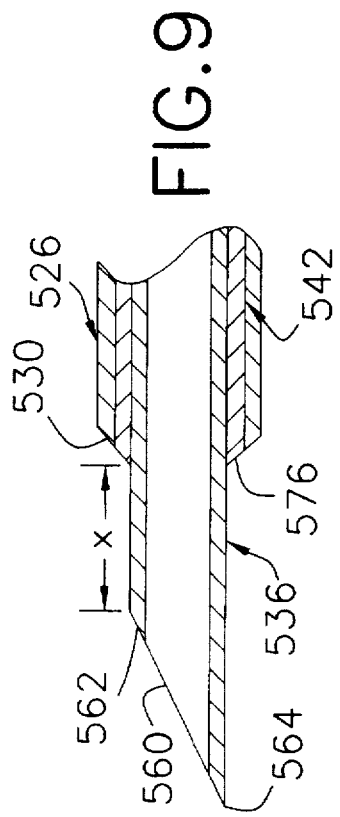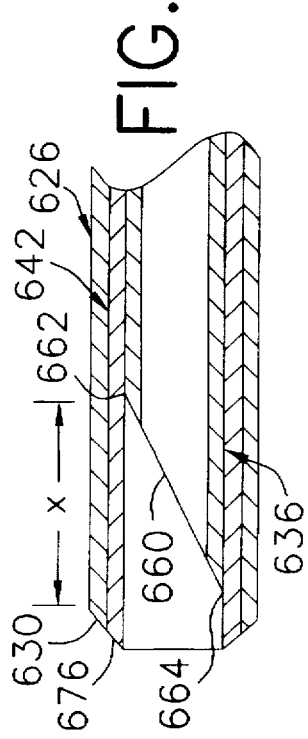

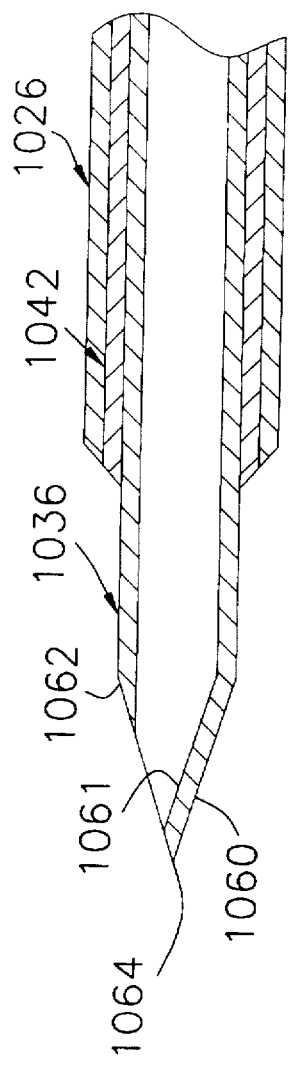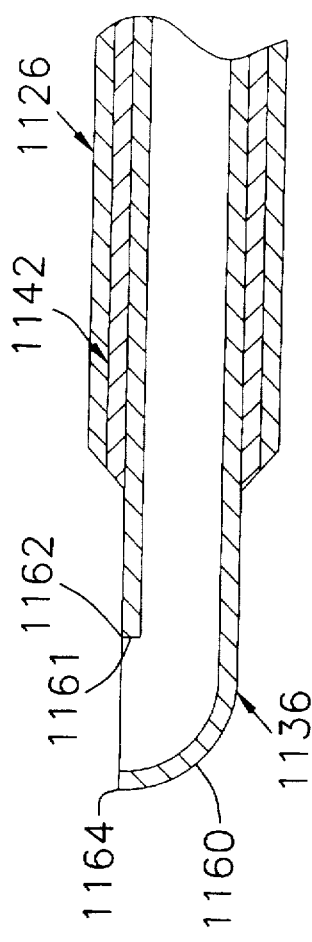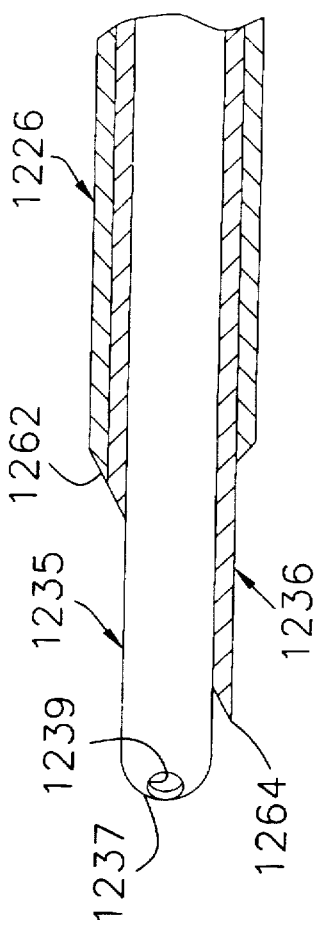

5,779,680

RETRACTABLE SAFETY NEEDLE INSTRUMENT WITH MOVABLE SAFETY MEMBER

CROSS-REFERENCE TO RELATED APPLICATIONS

This application is a continuation-in-part of applications Ser. No. 08/247,205, filed May 20, 1994, now U.S. Pat. No. 5,634,934, and Ser. No. 08/254,007, filed Jun. 3, 1994, now U.S. Pat. No. 5,478,317, which are a divisional application and a continuation application, respectively, of application Ser. No. 07/800,507, filed Nov. 27, 1991 and now abandoned; Ser. No. 08/079,586, filed Jun. 22, 1993, now U.S. Pat. No. 5,423,770, and Ser. No. 08/260,439, filed Jun. 15, 1994, now U.S. Pat. No. 5,423,760, which are divisional applications of application Ser. No. 07/868,578, filed Apr. 15, 1992 now U.S. Pat. No. 5,336,176; and Ser. No. 08/237,734, filed May 4, 1994, pending which is a continuation of application Ser. No. 07/868,578 Apr. 15, 1992, now U.S. Pat. No. 5,336,176. The disclosures of the above patent applications are incorporated herein by reference.

BACKGROUND OF THE INVENTION

1. Field of the Invention

The present invention pertains to safety needle instruments and, more particularly, to safety needle instruments including needles having sharp tips for penetrating anatomical tissue to establish communication with anatomical cavities wherein tissue and organ structures are protected from the tips of the needles.

2. Discussion of the Prior Art

Penetrating instruments are widely used in medical procedures to gain access to anatomical cavities ranging in size from the abdomen to small blood vessels, such as veins and arteries, epidural, pleural and subarachnoid spaces, heart ventricles and spinal and synovial cavities. Such penetrating instruments typically include an outer sleeve or cannula and a penetrating member disposed within the cannula and having a sharp tip for penetrating an anatomical cavity wall with the force required to penetrate the cavity wall being dependent upon the type and thickness of the tissue forming the cavity wall. Once the wall is penetrated, it is desirable to protect the sharp tip of the penetrating member from inadvertent contact with or injury to tissue or organ structures in or forming the cavity in that, once penetration is achieved, the lack of tissue resistance can result in the sharp tip traveling too far into the cavity and injuring adjacent tissue or organ structures.

Various safety penetrating instruments have been proposed, generally falling into protruding and retracting categories. In protruding safety penetrating instruments, a safety member is spring-biased to protrude beyond the tip of the penetrating member in response to the reduced force on the distal end of the safety member upon entry into the anatomical cavity. Safety needle instruments including a safety member in the form of a probe biased to protrude beyond the sharp tip of a needle have become widely accepted for use in penetrating anatomical cavities. For example, the Verres needle, commonly used to create a pneumoperitoneum, has a spring-loaded inner member disposed within a tubular needle. Safety trocars having a safety member in the form of a spring-biased protective shield disposed between an outer sleeve and an inner trocar are also known.

Retractable safety penetrating instruments typically include a trocar disposed within a portal sleeve and retractable within the sleeve in response to distally-biased movement of a component of the safety penetrating instrument, such as the trocar or the sleeve, caused by a reduction in force from tissue contact upon entering the anatomical cavity.

One of the limitations of many prior art safety needle instruments is that the safety probes can produce an irregular surface or profile with the sharp tips of the needles during penetration of tissue resulting in increased resistance during penetration of an anatomical cavity wall, trauma and damage to tissue and possible jamming of trapping of tissue. Another limitation of many prior art safety needle instruments is that very small or narrow anatomical cavities cannot be penetrated without protrusion of the safety probes from the sharp tips of the needles. A further limitation of many prior art safety needle instruments is that the needles cannot be automatically retracted to safe, protected positions wherein the sharp tips of the needles are disposed within the instruments upon penetration into anatomical cavities.

SUMMARY OF THE INVENTION

Accordingly, it is a primary object of the present invention to overcome the above disadvantages of the prior art and to improve safety needle instruments.

It is an additional object of the present invention to ease penetration of an anatomical cavity wall with a safety needle instrument by permitting penetrating components of the safety needle instrument, such as the cannula, safety shield and/or needle, to move proximally during penetration of the anatomical cavity wall and maintaining the movable penetrating components in substantially aligned positions such that a smooth distal profile is preserved during penetration of the anatomical cavity wall.

Another object of the present invention is to permit proximal movement of a safety shield and a needle of a safety needle instrument in response to tissue contact during penetration of an anatomical cavity wall.

A further object of the present invention is to permit proximal movement of a safety shield and a cannula of a safety needle instrument in response to tissue contact during penetration of an anatomical cavity wall.

Yet another object of the present invention is to permit proximal movement of a safety shield, cannula and needle of a safety needle instrument in response to tissue contact during penetration of an anatomical cavity wall.

A further object of the present invention is to trigger retraction of a needle of a safety needle instrument in response to distally-biased movement of the needle and a safety shield of the safety needle instrument upon entering an anatomical cavity.

An additional object of the present invention is to trigger retraction of a needle of a safety needle instrument in response to distally-biased movement of a safety shield and cannula of the safety needle instrument upon entering an anatomical cavity.

It is yet another object of the present invention to trigger retraction of a needle of a safety needle instrument in response to distally-biased movement of the needle and a cannula of the safety needle instrument upon entering an anatomical cavity.

Still another object of the present invention is to trigger retraction of a needle of a safety needle instrument in response to distally-biased movement of the needle, safety shield and cannula of the safety needle instrument upon entering an anatomical cavity.

Some of the advantages of the present invention over the prior art are that penetration of an anatomical cavity wall can be achieved using a smooth and continuous movement, that penetration of an anatomical cavity wall can be commenced with the cannula in an extended rest position either shielding or exposing the tip of the needle as desired, that the risk of developing a hematoma when penetrating veins and arteries is reduced, that the safety needle instrument can be used in many various ways including, for example, as an infusion or aspiration syringe, an intravenous needle system, an insufflation needle, a catheter system, a biopsy system, an injection or irrigation system, an aspiration or drainage system, catheterization for blood, urine, bile, ovarian fluid, spinal fluid, pleural fluid and bowel or peritoneal fluid sampling, and that retraction of the needle of the safety needle instrument can be achieved with a single trigger mechanism or with multiple trigger mechanisms for varying degrees of sensitivity such that the safety and efficacy of the safety needle instrument is enhanced.

The present invention is generally characterized in a safety needle instrument for establishing a portal in the wall of an anatomical cavity including a housing, a cannula fixedly secured to the housing, a needle disposed within the cannula and movable relative to the cannula between an extended position and a retracted position proximally spaced from the extended position, a distally-biased safety shield disposed between the cannula and the needle and movable relative to the cannula between an extended safety shield rest position protecting the needle distal end when the needle is retracted and a safety shield retracted position exposing the needle distal end when the needle is extended, retracting means for moving the needle from the needle extended position to the needle retracted position, means for manually moving the needle from the needle retracted position to the needle extended position, locking means for locking the needle in the needle extended position while permitting a predetermined amount of proximal movement of the needle during penetration of the anatomical cavity wall, needle bias means for biasing the needle distally in the locked needle extended position to permit the needle to move proximally during penetration of the anatomical cavity wall and distally upon introduction into the anatomical cavity, and releasing means responsive to penetration of the safety needle instrument into the anatomical cavity for triggering release of the locking means to permit the retracting means to move the needle to the needle retracted position.

Another aspect of the present invention is generally characterized in a safety needle instrument for establishing a portal in the wall of an anatomical cavity including a housing, a distally-biased cannula movable relative to the housing between an extended rest position and a proximally spaced retracted position, a needle disposed within the cannula and movable relative to the cannula between an extended position and a retracted position proximally spaced from the extended position, a distally-biased safety shield disposed between the cannula and the needle and movable relative to the needle between an extended safety shield rest position protecting the needle distal end when the needle is retracted and a safety shield retracted position exposing the needle distal end when the needle is extended, retracting means for moving the needle from the needle extended position to the needle retracted position, means for manually moving the needle from the needle retracted position to the needle extended position, locking means for locking the needle in the needle extended position and preventing proximal movement of the needle during penetration of the anatomical cavity wall, and releasing means responsive to penetration of the safety needle instrument into the anatomical cavity for triggering release of the locking means to permit the retracting means to move the needle proximally to the needle retracted position.

Yet another aspect of the present invention is generally characterized in a safety needle instrument for establishing a portal in the wall of an anatomical cavity including a housing, a distally-biased cannula movable relative to the housing between an extended rest position and a proximally spaced retracted position, a needle disposed within the cannula and movable relative to the cannula between an extended position and a retracted position proximally spaced from the extended position, a distally-biased safety shield disposed between the cannula and the needle and movable relative to the needle between an extended safety shield rest position protecting the needle distal end when the needle is retracted and a safety shield retracted position exposing the needle distal end when the needle is extended, retracting means for moving the needle from the needle extended position to the needle retracted position, means for manually moving the needle from the needle retracted position to the needle extended position, locking means for locking the needle in the needle extended position while permitting a predetermined amount of proximal movement of the needle during penetration of the anatomical cavity wall, needle bias means for biasing the needle distally in the locked needle extended position to permit the needle to move proximally during penetration of the anatomical cavity wall and distally upon introduction into the anatomical cavity, and releasing means responsive to penetration of the safety needle instrument into the anatomical cavity for triggering release of the locking means to permit the needle retracting means to move the needle proximally to the needle retracted position.

Other objects and advantages of the present invention will become apparent from the following description of the preferred embodiments taken in conjunction with the accompanying drawings wherein, unless specified otherwise, like parts or parts that perform like functions are identified in each of the several figures by the same reference numeral or by reference numerals sharing the same last two digits.

BRIEF DESCRIPTION OF THE DRAWINGS

FIG. 4 is a broken side view, partly in section, of a modification of a safety needle instrument according to the present invention.

FIG. 5 is a fragmentary side view, partly in section, of the distal end of the safety needle instrument of FIG. 4 following penetration into an anatomical cavity.

FIGS. 9–13 are fragmentary side views, partly in section, illustrating alternative distal configurations for the safety needle instruments of the present invention.

FIGS. 14 and 15 are fragmentary side views of alternative distal configurations for the needle of the safety needle instrument of the present invention.

FIG. 16 is a fragmentary side view, partly in section, of a safety probe for use with the safety needle instrument of the present invention.

DESCRIPTION OF THE PREFERRED EMBODIMENTS

Figure 1:
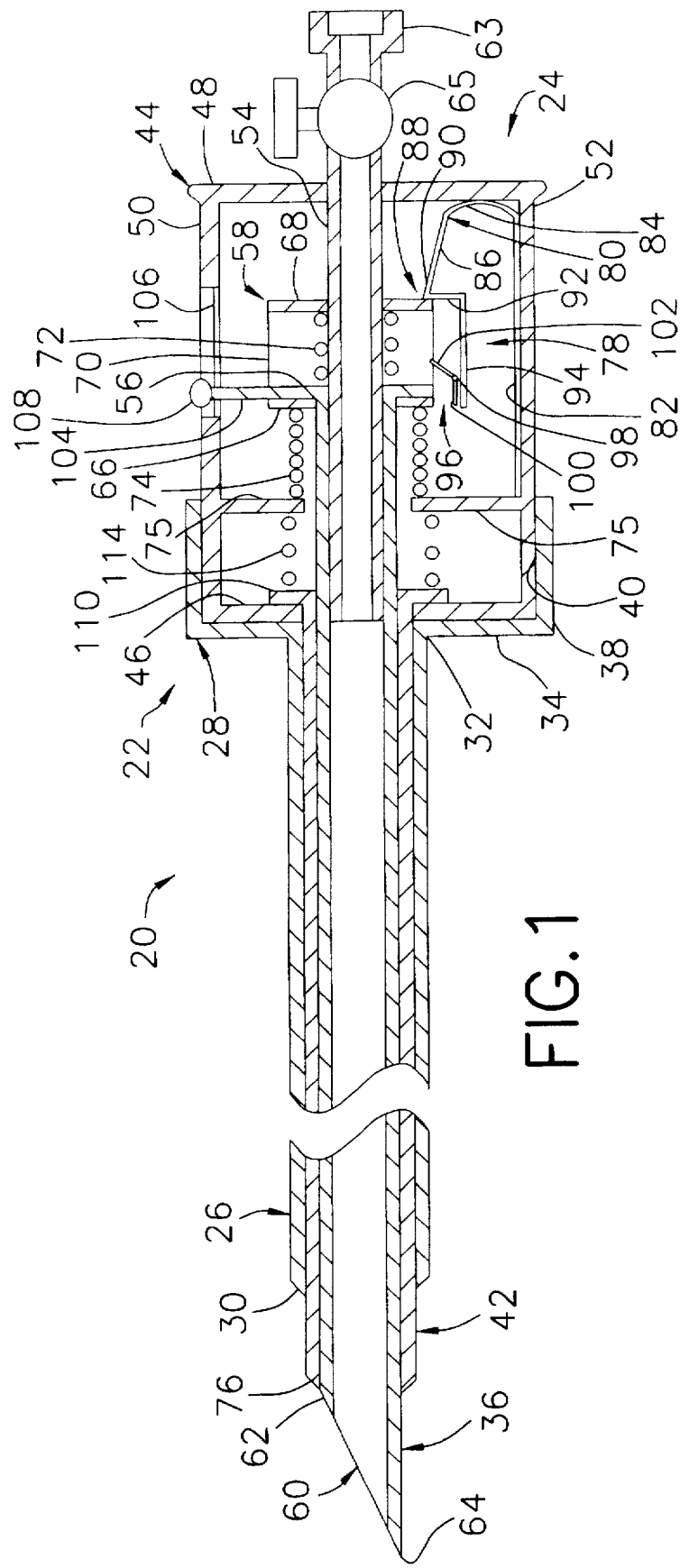
FIG. 1 is a broken side view, partly in section, of a safety needle instrument according to the present invention.

A safety needle instrument 20 according to the present invention, as shown in FIG. 1, includes a catheter unit 22 and a needle unit 24. The catheter unit 22 includes an elongate catheter or cannula 26 and a housing 28 mounting a proximal end of the cannula 26. Cannula 26 terminates distally at a distal end 30 and proximally at a proximal end 32 secured to a front wall 34 of the housing 28 and can have any desirable cross-sectional configuration, including cylindrical or tubular configurations, in accordance with the procedure to be performed and the anatomical cavity to be penetrated. Preferably, cannula 26 is made of a substantially cylindrical length of rigid or flexible and transparent or opaque material, such as a medically acceptable plastic or metal material, and has a tubular configuration defining a lumen between the distal and proximal cannula ends for receiving a needle 36 of needle unit 24.

Housing 28 can be made of any desirable material and can have any desirable configuration to facilitate grasping by a surgeon. As shown, the front wall 34 of the housing 28 is round and a generally cylindrical sidewall 38 extends proximally from the peripheral edge of the front wall in order to form a rearward facing recess 40 for receiving the needle unit 24. Recess 40 is preferably configured to telescopically receive and sealingly engage the distal end of the needle unit and other medical instruments, such as tubes, by friction fit, threaded engagement, Luer locks, detents or any other conventional coupling mechanism. Alternatively, cylindrical sidewall 38 can be configured for being received telescopically within a recess formed at the distal end of the needle unit or some other medical instrument. An opening is formed in the housing front wall 34 to allow passage therethrough by the needle 36 of needle unit 24; and, it will be appreciated that various valve mechanisms, such as trumpet or nipple valves, for example, can be disposed within the housing 28 for sealingly engaging instruments, such as the needle 36, that pass through the housing.

Needle unit 24 includes a hollow needle 36, a safety shield 42 and a hub 44 mounting proximal ends of the needle and the safety shield. Hub 44 includes longitudinally spaced front and rear walls 46 and 48 and laterally spaced top and bottom walls 50 and 52. Hub front wall 46 has a configuration to mate with the recess 40 of the housing; and, when the hub is mated with the housing as shown, safety shield 42 is disposed between the needle 36 and the cannula 26. Needle 36 is generally cylindrical and includes an elongate shaft or body telescopically fitted over a hollow guide tube 54 extending distally from the hub rear wall 48. The needle terminates proximally at a transverse flange 56 disposed between walls of a rail member 58 mounted in hub 44 and has an angled or beveled distal end 60 extending from a transverse dimensional transition or junction 62 in the shaft or body and terminating at a sharp distal tip 64. Guide tube 54 extends through the rear wall 48 of the hub to terminate proximally at a cylindrical coupling 63. Like recess 40, coupling 63 can be configured to sealingly engage the distal ends of medical instruments by friction fit, threaded engagement, Luer locks, detents or any other conventional coupling mechanism. A valve 65, shown as a stopcock valve, is disposed intermediate the coupling 63 and the hub rear wall 48 and can be used to control passage of fluids and objects through the guide tube and the needle.

Rail member 58 is generally U-shaped including a forward wall 66 disposed transverse or perpendicular to a longitudinal axis of the penetrating instrument, a rearward wall 68 in configuration parallel to forward wall 66 and a side wall 70 transversely joining the forward and rearward rail member walls. Flange 56 is disposed between the rail member forward and rearward walls with the rail member forward wall 66 having an opening therein allowing passage therethrough by the needle 36. The rail member forward and rearward walls are disposed parallel or substantially parallel to flange 56, and a bias member 72 is connected between needle flange 56 and the rail member rearward wall 68 to bias the needle distally. As shown, bias member 72 includes a helical coil spring disposed around the needle 36 and mounted in compression between flange 56 and the rail member rearward wall 68 to bias the needle 36 distally to cause flange 56 to abut the rail member forward wall 66. However, bias member 72 can include various other types of springs as well as other types of bias devices including compression springs, tension springs, torsion springs, pan springs, leaf springs, rubber, plastic or magnets, for example.

A retracting member 74 is mounted between rail member forward wall 66 and an inner wall or partition 75 within the hub proximally spaced from the front wall 46 of the hub to bias the needle 36 in a proximal direction to a retracted position where the distal end 60 of the needle is proximally spaced from the distal end 76 of the safety shield 42 as will be explained further below. The retracting member 74 includes a helical coil spring disposed around the needle 36 and mounted in compression between the rail member forward wall 66 and the hub partition 75 to bias the rail member 58, and therefore the needle 36, in a proximal direction to the retracted position where the distal end 60 of the needle is disposed proximally of the distal end 76 of the safety shield 42.

A locking and releasing mechanism 78 for locking the needle in an extended position, shown in FIG. 1, exposing the distal end 60 of the needle and for releasing the rail member 58 to allow the needle 36 to move to the retracted position includes a latch or locking spring 80, made of a strip of resilient material, formed to have a substantially flat base 82 secured to the bottom wall 52 of hub 44 and a bend 84 joining the proximal end of the base 82 with an upwardly angled arm 86 spaced from the base. Arm 86 carries or forms a latch 88 having a proximal angled latching surface 90 joining a distal latching surface 92 disposed substantially transverse to the longitudinal axis of the safety needle instrument and substantially parallel to the rail member rearward wall 68. Arm 86 has an extension 94 positioned distally of latch 88, and a releasing member or trigger 96 is juxtaposed with extension 94. The trigger 96 is pivotally mounted in the hub on a pin 98 secured to a wall or walls of the hub or structure supported in the hub, and the trigger is generally L-shaped with a leg 100 overlying extension 94 and a leg 102 extending transversely from leg 100 but at a slight angle toward the proximal end of the safety needle instrument. A torsion spring (not shown) is coiled around pin 98 and fixed to trigger 96 to bias the trigger counterclockwise, looking at FIG. 1, such that leg 100 is biased toward extension 94.

The needle flange 56 extends toward the top wall 50 of the hub and a post 104 extends from the needle flange through a longitudinal slot 106 formed in the top wall of the hub to terminate at a handle 108 disposed within an elongate trough-like recess 109. Handle 108, which can be coupled with the needle directly as shown or via the rail member, is grasped and manually moved distally along the slot formed in the top wall of the hub to move the needle from the retracted position to the locked extended position as previously explained above.

Safety shield 42 extends from distal end 76 to a proximal flange 110 disposed between the hub forward wall 46 and the inner wall or partition 75 proximally spaced from the hub forward wall. A bias member 114 in the form of a helical coil spring is disposed around the needle 36 and held in compression between the safety shield flange 110 and the hub partition 75 to bias the safety shield 42 distally toward a rest position where the safety shield flange abuts the hub forward wall.

The catheter unit 22 and the needle unit 24 can be provided separately or assembled together as shown in FIG. 1, and either or both of the portal and needle units can be manufactured in a manner to be disposable for single patient use or to be sterilizable for re-use. The hub 44 can be coupled to the housing 28 by suitable detent or latch mechanisms if desired, and the needle unit can be withdrawn from the catheter unit leaving the cannula 26 in place within an anatomical cavity to serve as a portal for the introduction or extraction of fluids therethrough.

Figure 3:
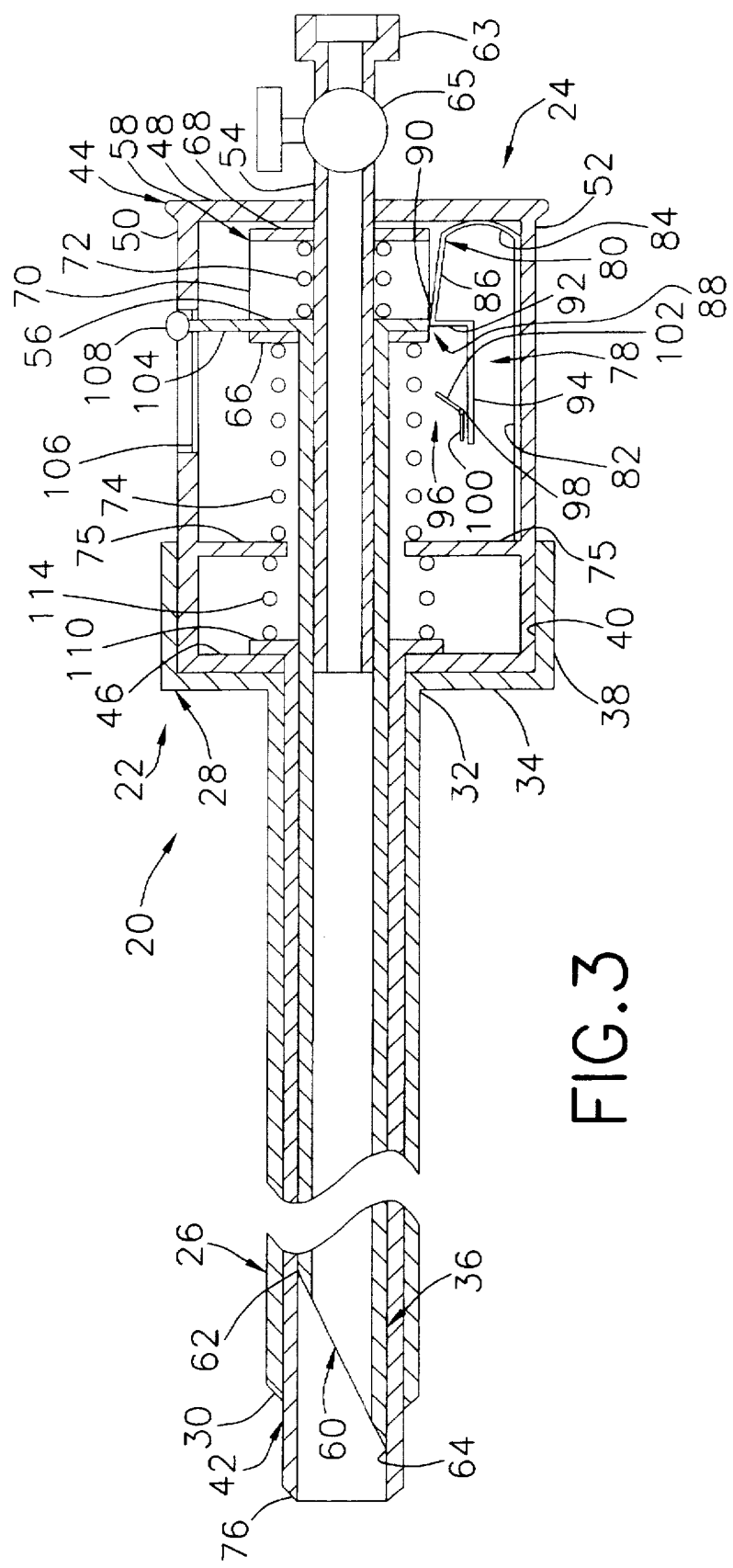
FIG. 3 is a broken side view, partly in section, of the safety needle instrument of FIG. 1 following penetration into the anatomical cavity.

In use, the safety needle instrument 20 can be provided in the condition illustrated in FIG. 3 with the safety shield 42 in the extended rest position and the needle 36 in the retracted position such that the distal end 60 of the needle is proximally spaced from the distal end 76 of the safety shield to protect the sharp tip 64 of the needle prior to use. In order to move the needle to the extended position shown in FIG. 1, the handle 108 is grasped to move the needle 36, and thus the rail member 58, distally until the rail member rearward wall 68 rides over latch 88 to be latched in the extended position with the rail member rearward wall 68 locked against distal latching surface 92. The user can feel the rail member rearward wall 68 lock into place in engagement with the latch 88 and can also visually determine that the needle is in the locked extended position by noting the position of the handle 108 at a distal end of the slot 106.

Figure 2:
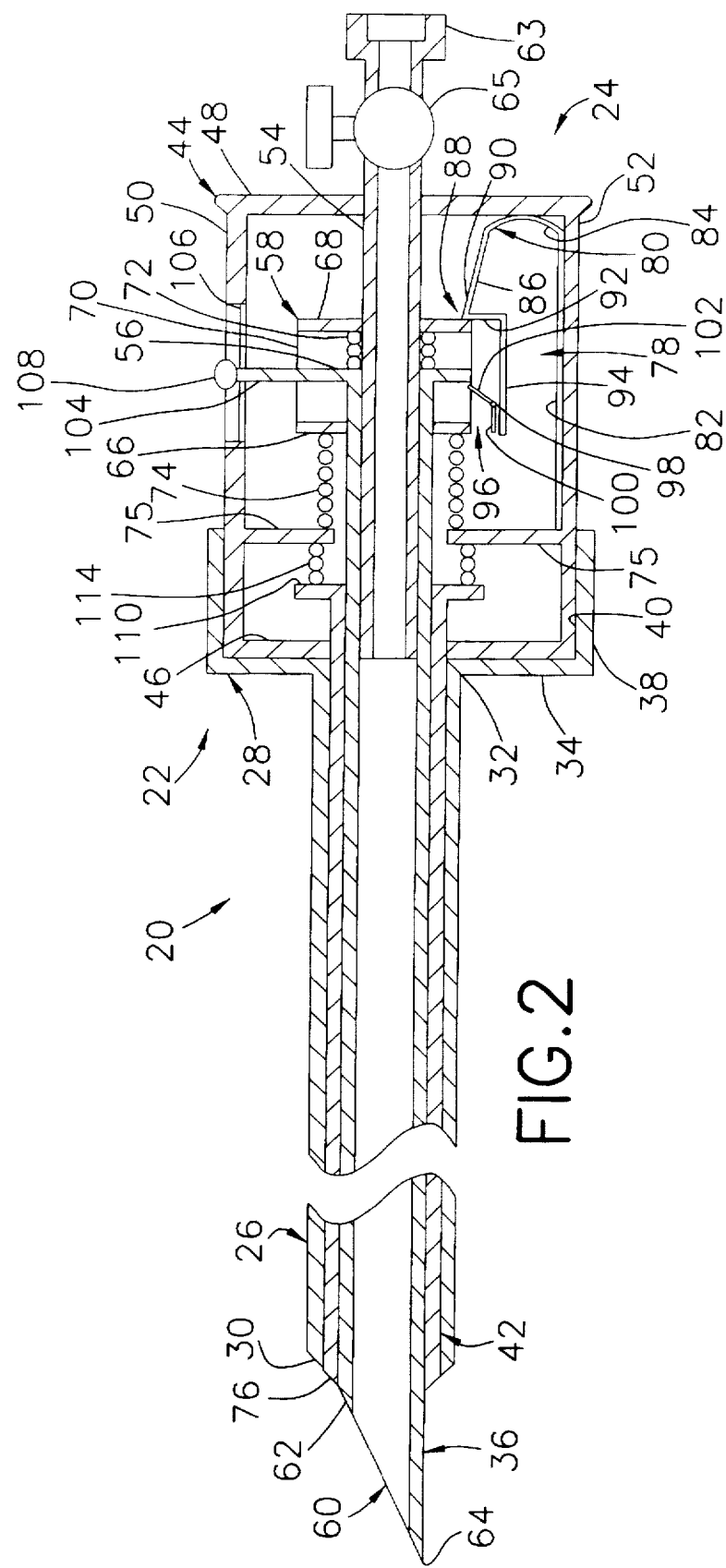
FIG. 2 is a broken side view, partly in section, of the safety needle instrument of FIG. 1 during penetration of a wall of an anatomical cavity.

With the needle 36 locked in the extended position illustrated in FIG. 1, the safety shield distal end 76 can be disposed proximally of the distal tip 64 of the needle in alignment with the transverse dimensional transition or junction 62 to present a smooth profile for penetrating tissue. Cannula distal end 30 is fixed and is proximally spaced from the safety shield distal end 76 a predetermined distance approximately equal to the distance between the partition and the hub front wall and between the rail member walls. Needle 36 can move proximally against the bias of bias member 72 in the extended position in response to forces acting on the needle distal end, such as the force from tissue contact during penetration of an anatomical cavity wall. Proximal movement of the needle is limited by engagement of the needle flange 56 with the rearward wall 68 of the rail member, which serves as a stop or abutment. Similarly, safety shield 42 can move proximally against the bias of bias member 114 in response to forces acting on the safety shield distal end 76 until the safety shield flange 110 abuts the hub partition 75. Since both the safety shield and the needle are free to move proximally in response to tissue resistance during penetration, the alignment of the safety shield distal end with the needle junction can be substantially maintained in order to ease penetration. When penetration of an anatomical cavity wall is commenced, therefore, the force from tissue contact on the safety shield and needle distal ends 76 and 60 will cause the safety shield and needle to move together proximally against the bias of respective bias members 114 and 72 towards becoming aligned with the cannula distal end 30. Needle flange 56 will also move past trigger leg 102 but will not cause movement of latch 88 since clockwise rotation of the trigger does not bring trigger leg 100 into contact with arm extension 94; and, since trigger 96 is biased in a counterclockwise direction, the trigger will return to its rest position and flange 56 will then be positioned proximally of trigger leg 102 as shown in FIG. 2.

Upon entry into the anatomical cavity, the counterforce on the safety shield and needle distal ends caused by tissue contact will be reduced allowing bias members 114 and 72 to move the safety shield and needle distally. Distal movement of the needle causes flange 56 to engage trigger leg 102 and to pivot the trigger counterclockwise looking at FIG. 2 causing leg 100 to engage arm extension 94. The engagement of leg 100 with arm extension 94 causes arm 86 to move toward base 82 moving the latch 88 out of engagement with the rail member rearward wall 68 thereby allowing the retracting member 74 to cause the needle to move proximally to the retracted position wherein the needle distal end 60 is proximally spaced from the safety shield distal end 76 to protect the sharp tip 64 of the needle as shown in FIG. 3. The needle unit 24 including the needle 36 can then be withdrawn from the catheter unit 22 leaving the cannula 26 in place within the anatomical cavity wall to serve as a portal for passage of fluids and medical instruments therethrough.

A modification of the safety needle instrument of the present invention is shown in FIG. 4 at 120. The modified safety needle instrument 120 includes a needle unit 124 identical to needle unit 24 for safety needle instrument 20 and a catheter unit 122 similar to catheter unit 22 but with a distally-biased cannula 126. Housing 128 for catheter unit 122 is similar to housing 28 but with an inner wall or partition 116 proximally spaced from the front wall 134 of the housing. Cannula 126 terminates proximally at a flange 132 disposed between the front wall 134 of the housing 128 and the inner wall or partition 116. A bias member 118 in the form of a helical coil spring is disposed around the safety shield 142 and held in compression between the cannula flange 132 and the housing partition 116 to bias the cannula distally toward a rest position where the cannula flange 132 abuts the front wall 134 of the housing and the distal end 130 of the cannula is aligned with the distal end 176 of the safety shield and the junction 162 of the extended needle 136.

Use of the safety needle instrument 120 for penetrating an anatomical cavity wall proceeds essentially as described above for safety needle instrument 20 with the exception that the cannula 126 will move proximally in response to tissue contact and distally upon entering the anatomical cavity. Prior to contacting the anatomical cavity wall, the needle 136 is manually moved distally to be locked in the extended position and distal ends 130 and 176 of the cannula 126 and safety shield 142 are in rest positions aligned with the junction 162 at the distal end of the extended needle as shown in FIG. 4. During penetration, the cannula 126, needle 136 and safety shield 142 can be moved proximally due to the force from tissue contact such that the smooth distal profile can be substantially maintained in order to ease penetration. Upon penetrating into the anatomical cavity, the counterforce on the distal ends of the cannula, needle and safety shield are reduced allowing the respective bias members to move the cannula, needle and safety shield distally. As shown, distally-biased movement of the needle triggers release of the needle from the locked extended position allowing the needle to be moved proximally to a retracted position where the distal end of the needle is proximally spaced from both the cannula and safety shield distal ends as shown in FIG. 5.

Figure 6:
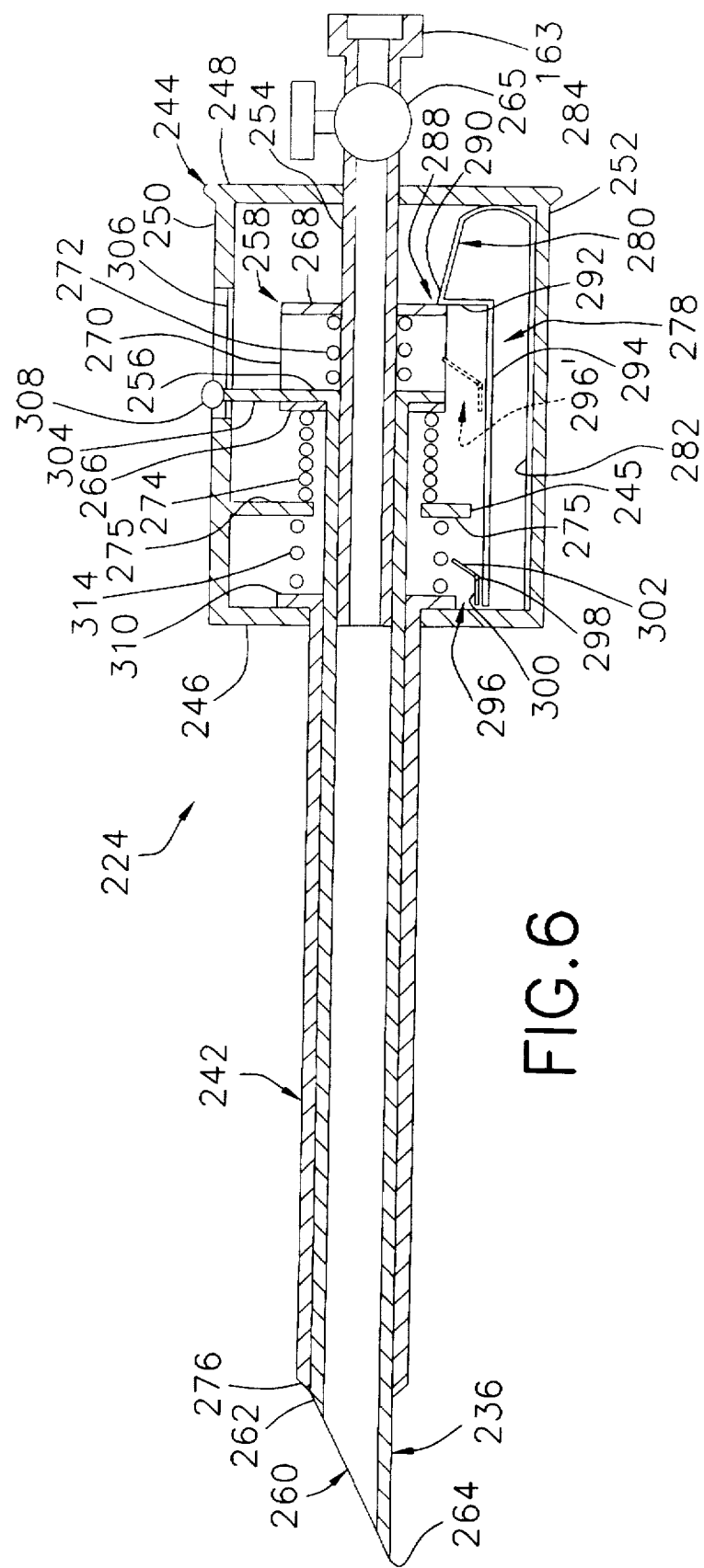
FIG. 6 is a side view, partly in section, of a modified needle unit for the safety needle instrument according to the present invention.

A modified needle unit for use with the safety needle instruments of the present invention is shown in FIG. 6 at 224. The modified needle unit 224 includes a hub 244 mounting proximal ends of a needle 236 and a safety shield 242. Hub 244 is similar to hub 44 for safety needle instrument 20 but with an opening or gap 245 formed in the hub partition 275 on the side of the hub mounting a locking and releasing mechanism 278. Arm extension 294 for needle unit 224 extends distally from a distal latching surface 292 through the opening 245 to be disposed alongside the safety shield flange 310. A trigger 296, similar to trigger 96 for safety needle instrument 20, is distally spaced from hub partition 275 and is pivotally mounted on a pin 298 secured to a wall or walls of the hub between arm extension 294 and the safety shield flange 310. Trigger 296 is generally L-shaped with a leg 300 overlying extension 294 and a leg 302 extending transversely from leg 300 and toward the proximal end of the hub to be disposed proximally of the safety shield flange 310 when the safety shield is in the extended rest position shown.

Prior to use, needle unit 224 can be coupled with a catheter unit, such as catheter unit 22, for establishing a portal in the wall of an anatomical cavity. Operation of the needle unit 224 is similar to that of needle unit 24 with the exception that distally-biased movement of the safety shield 242 in response to a reduction in force caused by tissue contact is used to trigger release of the latch 288 from the rail member rearward wall 268 so that the needle 236 is moved proximally to the retracted position when the safety shield enters the anatomical cavity.

Another modification of the needle unit of the safety needle instrument according to the present invention is arrived at by mounting a second trigger in the needle unit 224, as shown in phantom at 296' in FIG. 6. The second trigger 296' is mounted within the hub 244 at a location similar to that of trigger 96 in needle unit 24 for being engaged by the needle flange 256. By providing a second trigger proximate the needle flange 256, movement of the needle to the retracted position can be achieved in response to distally-biased movement of either or both of the safety shield and the needle upon entering an anatomical cavity. Operation of the modified needle unit is similar to that described above in connection with needle unit 224 with the exception that safety shield and needle flanges are moved to positions proximally spaced from triggers 296 and 296' during penetration of an anatomical cavity wall and will move distally in response to a reduction in force from tissue contact upon entering the anatomical cavity. Distally-biased movement of either or both of the safety shield 242 and needle 236 causes one or both triggers to be rotated counterclockwise looking at FIG. 6 such that arm extension 294 of the locking spring 280 will be moved away from the longitudinal axis of the needle unit toward the base 282 of the locking spring to release latch 288 from the rail member 258. Retraction of the needle can thus be assured even if one of the penetrating components is prevented from moving distally upon entering the anatomical cavity.

Figure 7:
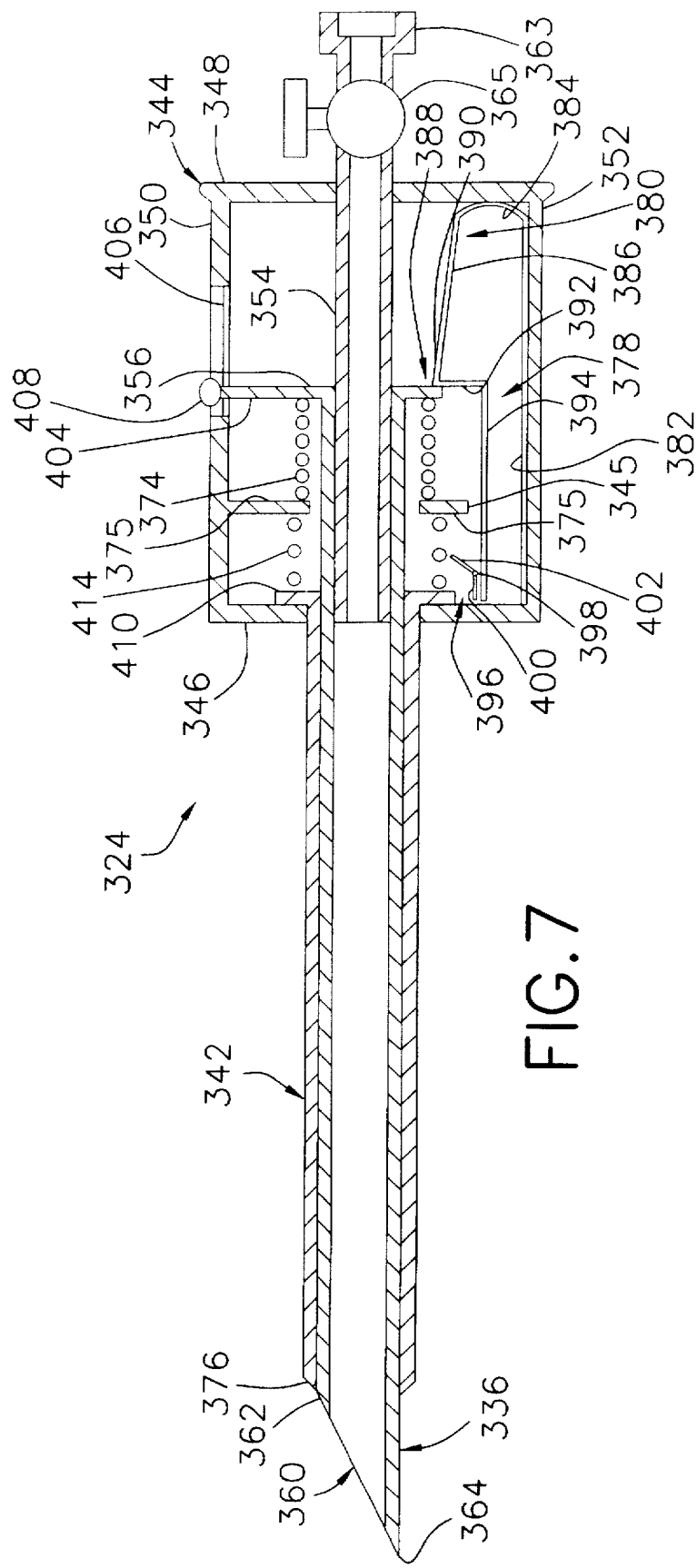
FIG. 7 is a side view, partly in section, of still another modified needle unit for the safety needle instrument according to the present invention.

FIG. 7 illustrates another modified needle unit for a safety needle instrument according to the present invention wherein the modified needle unit 324 is similar to needle unit 224 described above but with a locking mechanism that prevents proximal movement of the needle in response to tissue contact during penetration of an anatomical cavity wall. The locking spring 380 of the locking and releasing mechanism 378 for needle unit 324 is the same as locking spring 280 for needle unit 224; however, the needle 336 is not mounted by a rail member and is instead directly engaged by distal latching surface 392 formed by the locking spring 380. Retracting member 374 for needle unit 324 is disposed around the needle 336 and is held in compression between the hub partition 375 of the hub 344 and the needle flange 356 to bias the needle proximally against latching surface 392 when the needle is in the extended position shown and to move the needle to the retracted position when the latch 388 is released. As a result, needle 336 is fixed during penetration and will move proximally to the retracted position only in response to distally-biased movement of the safety shield 342 upon entering the anatomical cavity.

Figure 8:
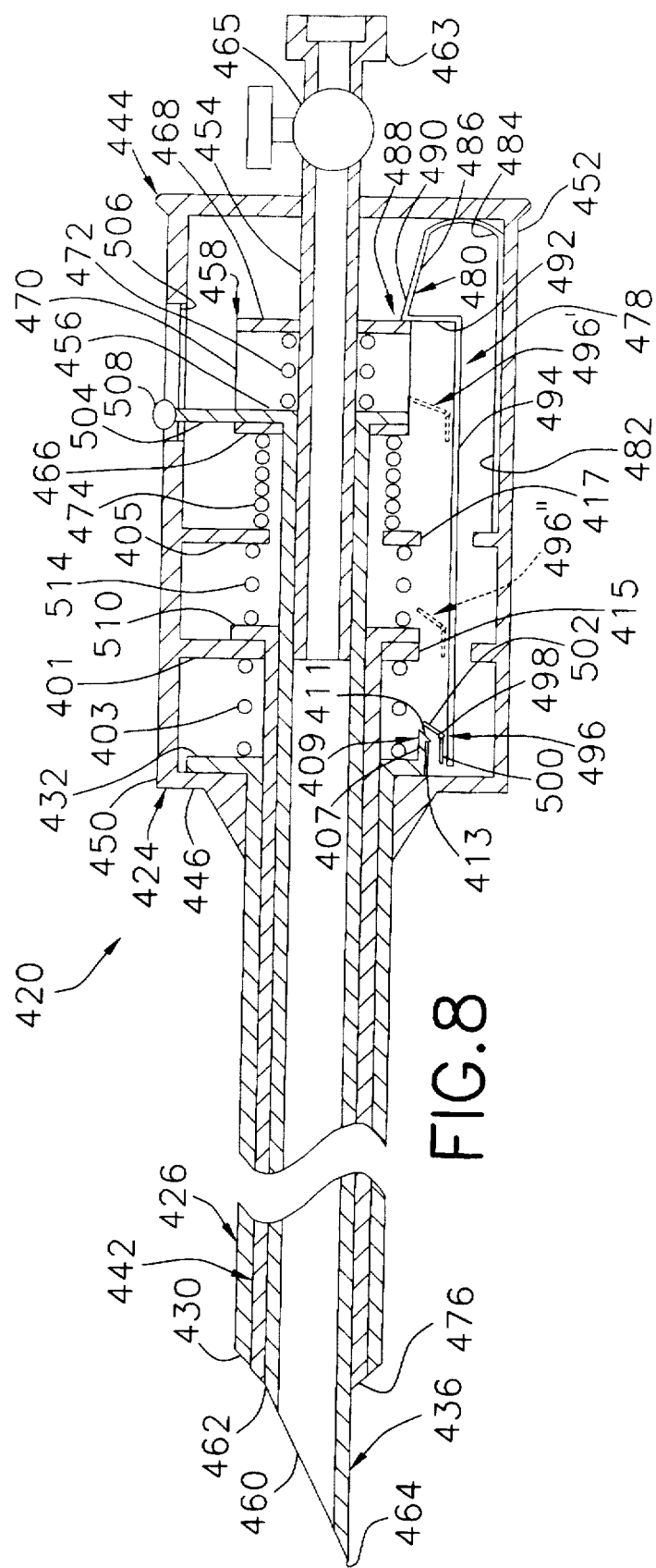
FIG. 8 is a broken side view, partly in section, of a further modification of a safety needle instrument according to the present invention.

Still another modification of the safety needle instrument according to the present invention is illustrated in FIG. 8 at 420. The modified safety needle instrument 420 is similar to safety needle instrument 120 except that movement of the needle to the retracted position is triggered by distally-biased movement of the cannula in response to a reduction in the force from tissue contact following entry into the anatomical cavity. Safety needle instrument 420 includes only a needle unit 424 having a cannula 426, a needle 436, a safety shield 442 and a hub 446 mounting proximal ends of the cannula, needle and safety shield. Needle 436 is similar to needle 36 and terminates distally at a distal end 460 and proximally at a transverse flange 456 disposed between forward and rearward walls 466 and 468 of a rail member 458 disposed within the hub. The proximal end of the needle 436 is telescopically fitted over a hollow guide tube 454 extending through the rear wall 448 of the hub 444 to join with a valve 465 and a coupling 463 proximally spaced from the hub rear wall. The bias member 472 is similar to bias member 72 and is disposed around the guide tube 454 and held in compression between the needle flange 456 and the rearward wall of rail member 458 to bias the needle in a distal direction relative to the rail member. Cannula 426 is similar to cannula 126; however, flange 432 at the proximal end of the cannula is disposed between the hub front wall 466 and a first inner wall or partition 401 proximally spaced from the hub front wall perpendicular to a longitudinal axis of the safety needle instrument. Bias member 403 for cannula 426 is disposed around the safety shield 442 and is held in compression between the first hub partition 401 and the cannula flange 432 to bias the cannula in a distal direction toward an extended rest position where the cannula flange abuts the hub front wall 446. Safety shield 442 is similar to safety shield 142 and includes a flange 410 disposed between the first inner wall or partition 401 of the hub and a second inner wall or partition 405 proximally spaced from the first hub partition. Bias member 414 for safety shield 442 is disposed around the needle 436 and is held in compression between the second hub partition 405 and the safety shield flange 410 to bias the safety shield distally toward an extended rest position where the safety shield flange abuts the first hub partition 401. A retracting member 474, similar to retracting member 174, is also disposed around the needle 436 but is held in compression between the rail member forward wall 456 and the second hub partition 405.

A finger 407 extends proximally from the cannula flange 432 in the direction of partition 401 and carries an outwardly oriented barb or pawl 409 at a proximal end having an angled proximal surface 411 and a transverse or vertical surface 413 substantially parallel to flange 432. An opening or gap 415 is formed in the hub partition 401 on the side of the hub mounting the locking and releasing mechanism 478 and is of an appropriate size and shape to permit passage of the finger 407 when the cannula 426 is moved. A similar opening 417 is formed in the second hub partition 405 in axial alignment with the first opening 415. Locking and releasing mechanism 478 for the safety needle instrument 420 is similar to locking and releasing mechanism 178 for safety needle instrument 120 except that arm extension 494 for safety needle instrument 420 extends distally from a distal latching surface 492 through openings 415 and 417 to be disposed alongside the finger 407 carried by the cannula flange 432. A trigger 496, similar to trigger 196 for safety needle instrument 120, is distally spaced from hub partition 401 and is pivotally mounted on a pin 498 secured to a wall or walls of the hub between arm extension 494 and the cannula flange 432. Trigger 496 is generally L-shaped with a leg 400 overlying extension 494 and a leg 402 extending transversely from leg 400 and toward the proximal end of the hub to be disposed proximally of the barb 409 at the proximal end of finger 407 when the cannula is in the extended rest position shown.

Operation of the safety needle instrument 420 is similar to that of safety needle instrument 120 with the exception that proximal movement of the cannula 426 in response to the force from tissue contact causes barb 409 to engage trigger leg 402 rotating the trigger 496 clockwise looking at FIG. 8. Trigger leg 400 is thus moved away from arm extension 494 such that latch 488 maintains the rail member 458 in the extended position and barb 409 is then positioned proximally of trigger leg 402. Upon penetrating into an anatomical cavity, distally-biased movement of the cannula 426 in response to a reduction in force caused by tissue contact causes the transverse surface 413 of the barb 409 to move distally into engagement with the trigger leg 402 causing the trigger 496 to rotate counterclockwise looking at FIG. 8 triggering release of the latch 488 from the rail member rearward wall 468 so that the needle 436 is moved proximally to the retracted position by retracting member 474 when the cannula enters the anatomical cavity.

Another modification of the safety needle instrument of the present invention is arrived at by mounting a second trigger in the needle unit 424, as shown in phantom at 496' in FIG. 8. The second trigger 496' is mounted within the hub 444 at a location similar to that of trigger 196 in needle unit 24 for being engaged by the needle flange 456. By providing a second trigger proximate the needle flange 456, movement of the needle to the retracted position can be achieved in response to distally-biased movement of either or both of the cannula and the needle upon entering an anatomical cavity. Operation of the modified needle unit is similar to that described above in connection with needle unit 424 with the exception that cannula and needle flanges are moved to positions proximally spaced from triggers 496 and 496' during penetration of an anatomical cavity wall and will move distally in response to a reduction in force from tissue contact upon entering the anatomical cavity. Distally-biased movement of either or both of the cannula 426 and the needle 436 causes one or both triggers to be rotated counterclockwise looking at FIG. 8 such that arm extension 494 of the locking spring 480 will be moved away from the longitudinal axis of the needle unit toward the base 482 of the locking spring to release latch 488 from the rail member 458. Retraction of the needle can thus be assured even if one of the penetrating components is prevented from moving distally upon entering the anatomical cavity. Alternatively, or in addition to mounting the second trigger 496', it will be appreciated that a third trigger, shown in phantom in FIG. 8 at 496", can be mounted proximate the safety shield flange 410 for disengaging the latch 488 in response to distally-biased movement of the safety shield in response to a reduction in force from tissue contact.

FIG. 9 shows an alternative distal configuration for the safety needle instruments of the present invention wherein the distal end 576 of the safety shield 542 and the distal end 530 of the cannula 526 are proximally spaced from the distal end junction 562 of the needle 536 a predetermined distance x when the safety shield and cannula are in rest positions and the needle is locked in the extended position. In this configuration, the needle can move proximally during penetration towards becoming aligned with the cannula and safety shield distal ends to ease penetration by providing a smooth profile and can either stop or move together with the safety shield and cannula as penetration continues. Upon entering into an anatomical cavity, the safety shield, needle and/or cannula can spring back distally triggering release of the latch holding the needle to permit the retracting member to move the needle proximally to the retracted position where the sharp tip 564 of the needle is protected.

FIG. 10 shows another alternative distal configuration for the safety needle instruments of the present invention wherein the distal end 676 of the safety shield 642 and the distal end 630 of the cannula 626 are distally spaced from the distal end junction 662 of the needle 636 a predetermined distance x when the safety shield and cannula are in rest positions and the needle is locked in the extended position. In this configuration, the safety shield and cannula can move proximally during penetration towards becoming aligned with the needle junction to ease penetration by providing a smooth profile and can move together with the needle as penetration continues. Upon entering into an anatomical cavity, the safety shield, needle and/or cannula can spring back distally triggering release of the latch holding the needle to permit the retracting member to move the needle proximally to the retracted position where the sharp tip 664 of the needle is protected.

Still another distal configuration for the safety needle instruments of the present invention is shown in FIG. 11 wherein the distal end 776 of the safety shield 742 is distally spaced from the cannula distal end 730 and the distal end junction 762 of the needle 736 a predetermined distance x when the cannula and safety shield are in rest positions and the needle is locked in the extended position. In this configuration, the safety shield can move proximally during penetration towards becoming aligned with the cannula distal end and the needle distal end junction to ease penetration by providing a smooth profile and can move together with the needle and/or cannula as penetration continues. Upon entering into an anatomical cavity, the needle, cannula and/or safety shield can spring back distally triggering release of the latch holding the needle to permit the retracting member to move the needle proximally to the retracted position where the sharp tip 764 of the needle is protected.

Another distal configuration for the safety needle instruments of the present invention is shown in FIG. 12 wherein the distal end 830 of the cannula 826 is distally spaced from both the safety shield distal end 876 and the distal end junction 862 of the needle 836 a predetermined distance x when the cannula and safety shield are in rest positions and the needle is locked in the extended position. In this configuration, the cannula can move proximally during penetration towards becoming aligned with the safety shield distal end and the needle distal end junction to ease penetration by providing a smooth profile and can move together with the needle and/or safety shield as penetration continues. Upon entering into an anatomical cavity, the needle, safety shield and/or cannula can spring back distally triggering release of the latch holding the needle to permit the retracting member to move the needle proximally to the retracted position where the sharp tip 864 of the needle is protected.

An additional distal configuration for the safety needle instruments of the present invention is shown in FIG. 13 wherein the distal end 976 of the safety shield 942 is proximally spaced from the distal end 930 of the cannula 926 and the junction 962 of the needle 936 a predetermined distance x when the cannula and safety shield are in rest positions and the needle is locked in the extended position. In this configuration, the needle and cannula can move proximally during penetration towards becoming aligned with the safety shield distal end to ease penetration by providing a smooth profile and can move together with the safety shield as penetration continues. Upon entering into an anatomical cavity, the needle, safety shield and/or cannula can spring back distally triggering release of the latch holding the needle to permit the retracting member to move the needle proximally to the retracted position where the sharp tip 964 of the needle is protected.

From the above, it will be appreciated that multiple penetrating components of the safety needle instrument of the present invention are movable proximally during penetration of an anatomical cavity wall and are biased to move distally upon entering the anatomical cavity. By "penetrating components" is meant those elements of the safety needle instrument that enter an anatomical cavity, such as the cannula, safety shield and needle of the safety needle instrument; and retraction of the needle to a position where the distal end of the needle is protected can be conditioned upon distally-biased movement of one or more of the movable penetrating components, such as the cannula, the safety shield and/or the needle, depending on the type and number of locking and releasing mechanisms provided. Furthermore, distal ends of the cannula, the safety shield and/or the needle can be aligned prior to penetration to define a smooth distal profile for penetrating anatomical tissue, and can be substantially maintained in alignment during penetration by permitting proximal movement of the needle, cannula and/or safety shield. Alternatively, the distal ends of the cannula and/or the safety shield can be distally or proximally spaced from the needle distal end such that movement of the cannula, safety shield and/or needle in response to tissue contact will cause the distal ends of the cannula, safety shield and needle to become aligned. If the cannula and/or safety shield distal ends are distally spaced from the needle distal end in the extended rest position, the cannula and/or safety shield can also function as safety members to protect the needle distal end even in the event that the needle is not retracted.

The components of the safety needle instrument of the present invention can be made of any suitable, medical grade materials to permit sterilization for re-use or for single patient use. The components can be made of multiple parts of various configurations and materials to reduce cost. The catheter unit and needle unit can have various valves, stop cocks and seals to control fluid flow therethrough, and conventional detent mechanisms can be used to connect or latch the hub with the housing when the catheter unit and the needle unit are assembled. The distal end of the cannula can be chamfered or blunt, smooth or roughened, or have any other configuration depending on the need for ease of penetration or increased resistance. Also, the strength of the bias members biasing the cannula, safety shield and/or needle can be chosen according to differences in the resistant forces acting on the cannula, safety shield and needle in order to maintain a smooth distal profile during penetration.

The distal end of the needle can have any desired configuration suitable for defining a distal opening and for penetrating anatomical tissue, such as, for example, the beveled or slanted configuration shown and described, a conical or pyramidal distal configuration 1060 with an aperture or opening 1061 on the tapered portion of the distal end as shown in FIG. 14, or a curved distal end 1160 with a transverse or side-facing opening 1161 as shown in FIG. 15. Additionally, the surface defining the distal end of the needle can be irregular or smooth, continuous or disjointed, provided with cutting features or having any combination of the above.

FIG. 16 shows a modification of the safety needle instrument of the present invention wherein the modified safety needle instrument 1220 has a cannula 1226 surrounding a hollow needle 1236 and a cylindrical safety probe 1235 disposed within the needle and movable between an extended protruding position protecting the distal end 1260 of the needle and a retracted position exposing the distal end of the needle. The safety probe is distally biased and has a rounded distal end 1237 with an opening or aperture 1239 formed therein for permitting passage of fluids through the needle. It will be appreciated that the safety probe can be mounted in the hub or housing of any of the safety needle instruments shown and that a flange or other type of protrusion can be carried at the safety probe proximal end and either passed through a slot or opening in the needle or disposed proximally of the rail member to serve as an operating member for triggering retraction of the needle in response to distally-biased movement of the probe in response to a reduction in force caused by tissue contact upon entering an anatomical cavity. The safety probe distal end can have any configuration to protrude through single or multiple openings formed in the distal end of the needle and can conform to the distal profile of the needle when retracted or present a discontinuous surface when retracted.

The rail member can have various configurations to engage the latch and be released by the trigger. Preferably, the rail member will have a configuration to serve as a stop or abutment for the needle as exemplified herein by a U-shaped rail member.

The locking and releasing mechanisms require only a latch for locking the needle in the extended position and a trigger for releasing the latch in response to distal movement of an operating member such as a flange carried by the needle, cannula, safety shield and/or a probe; and, thus, it will be appreciated that various mechanisms can be employed to produce the locking and releasing functions such as, for example, multiple movably or pivotally mounted cams or pawls. It will be appreciated that the locking and releasing mechanism can be designed and arranged in the housing or the hub in various ways to minimize the length of the housing or the hub and, therefore, the overall length of the housing and hub. Various locking and releasing mechanisms that can be simply modified for use in the safety needle instrument of the present invention are disclosed in U.S. Pat. Nos. 5,330,432; 5,324,268; 5,320, 610; 5,336,176; and 5,360,405 to Yoon and Applicant's pending applications Ser. No. 07/848,838, filed Mar. 10, 1992; Ser. No. 07/845,177, filed Sep. 15, 1992; Ser. No. 07/945,177, filed Sep. 15, 1992; Ser. No. 08/079,586, filed Jun. 22, 1993; Ser. No. 08/195,512, filed Feb. 14, 1994; Ser. No. 08/196,029, filed Feb. 14, 1994; Ser. No. 08/196,027, filed Feb. 14, 1994; Ser. No. 08/195,178, filed Feb. 14, 1994; Ser. No. 08/237,734, filed May 4, 1994; Ser. No. 08/247,205, filed May 20, 1994; Ser. No. 08/254,007, filed Jun. 3, 1994; and Ser. No. 08/260,439, filed Jun. 15, 1994. The disclosures of the above-listed issued patents and pending patent applications are incorporated herein by reference. The issued patents and applications listed above also disclose various bias arrangements useful with the safety needle instrument of the present invention. Other locking and releasing mechanisms that can be used in the safety needle instrument of the present invention are disclosed in Applicant's pending applications Ser. Nos. 08/279,170 and 08/279,172, filed Jul. 22, 1994, the disclosures of which are incorporated herein by reference.

One or more control buttons, such as the control buttons described in Applicant's copending patent application, Ser. No. 08/083,220, filed Jun. 24, 1993, can be mounted next to any latch for manually disengaging the latch to prevent locking of the needle in the extended position. Furthermore, additional latches can be provided or existing latches modified to carry pawls or form latching surfaces for locking a needle in the retracted position and can then be released through the use of a control button as described above to permit the needle to be moved distally to the locked extended position prior to use.

It will also be appreciated that after penetration of the safety needle instrument into the anatomical cavity, the distally-biased cannula and/or safety shield can act as a shock absorber upon inadvertent contact with tissue. The distal bias for the triggering member (i.e., the cannula, needle, safety shield and/or probe) of the safety needle instrument need only be strong enough to allow slight movement of the member during penetration such that the force-to-penetrate can be minimized.

The features of the various embodiments described above can be combined in any manner desired dependent upon the requirements and complexity of the safety needle instrument.

Inasmuch as the present invention is subject to many variations, modifications and changes in detail, it is intended that all subject matter discussed above or shown in the accompanying drawings be interpreted as illustrative only and not be taken in a limiting sense.

What is claimed is:

1. A safety needle instrument for establishing a portal in the wall of an anatomical cavity comprising a housing;

an elongate cannula having a proximal end mounted by said housing and a distal end for introduction in the anatomical cavity;

a needle disposed within said cannula and having a distal end for penetrating the anatomical cavity wall, said needle being movable relative to said cannula between an extended position where said distal end of said needle protrudes distally from said distal end of said cannula and a retracted position proximally spaced from said extended position;

a safety shield disposed between said cannula and said needle, said safety shield being movable relative to said cannula between an extended safety shield rest position protecting said needle distal end when said needle is retracted and a safety shield retracted position exposing said needle distal end when said needle is extended;

safety shield bias means for biasing said safety shield distally toward said safety shield rest position;

retracting means for moving said needle from said needle extended position to said needle retracted position;

means for manually moving said needle from said needle retracted position to said needle extended position;

locking means for locking said needle in said needle extended position while permitting a predetermined amount of proximal movement of said needle during penetration of the anatomical cavity wall;

needle bias means for biasing said needle distally in said locked needle extended position to permit said needle to move proximally during penetration of the anatomical cavity wall and distally upon introduction into the anatomical cavity; and releasing means responsive to penetration of said safety needle instrument into the anatomical cavity for triggering release of said locking means to permit said retracting means to move said needle to said needle retracted position.

2. A safety needle instrument as recited in claim 1 wherein said releasing means is responsive to distally-biased movement of said needle upon penetrating into the anatomical cavity.

3. A safety needle instrument as recited in claim 1 wherein said releasing means is responsive to distally-biased movement of said safety shield upon penetrating into the anatomical cavity.

4. A safety needle instrument as recited in claim 1 wherein said releasing means is responsive to distally-biased movement of said cannula and said needle upon penetrating into the anatomical cavity.

5. A safety needle instrument as recited in claim 1 wherein said needle distal end extends distally from a junction where a transverse dimension of said needle changes and wherein said safety shield distal end is aligned with said junction when said safety shield is in said rest position and said needle is in said locked needle extended position.

6. A safety needle instrument as recited in claim 1 wherein said needle distal end extends distally from a junction where a transverse dimension of said needle changes and wherein said safety shield distal end is located proximally of said junction when said safety shield is in said rest position and said needle is in said locked needle extended position.

7. A safety needle instrument as recited in claim 1 wherein said needle distal end extends distally from a junction where a transverse dimension of said needle changes and wherein said safety shield distal end is located distally of said junction when said safety shield is in said rest position and said needle is in said locked needle extended position.

8. A safety needle instrument as recited in claim 2 and further comprising a rail member mounting a proximal end of said needle, wherein said proximal end of said needle includes a flange movable within said rail member and said locking and releasing mechanism includes a latch spring engaging said rail member to lock said needle in said extended position and a trigger responsive to distally-biased movement of said needle flange for releasing said latch spring.

9. A safety needle instrument as recited in claim 3 and further comprising a rail member mounting a proximal end of said needle, wherein said proximal end of said needle includes a flange movable within said rail member, said proximal end of said safety shield includes an operating member, and said locking and releasing mechanism includes a latch spring for engaging said rail member to lock said needle in said extended position and a trigger responsive to distally-biased movement of said operating member for releasing said latch spring.

10. A safety needle instrument as recited in claim 4 and further comprising a rail member mounting a proximal end of said needle, wherein said proximal end of said needle includes a flange movable within said rail member, said proximal end of said safety shield includes an operating member, and said locking and releasing mechanism includes a latch spring for engaging said rail member to lock said needle in said extended position and a trigger responsive to distally-biased movement of said operating member and needle flange for releasing said latch spring.

11. A safety needle instrument for establishing a portal in the wall of an anatomical cavity comprising

- a housing;
- an elongate cannula having a proximal end mounted by said housing and a distal end for introduction in the anatomical cavity, said cannula being movable relative to said housing between an extended rest position and a proximally spaced retracted position;
- cannula bias means for biasing said cannula distally toward said cannula rest position;
- a needle disposed within said cannula and having a distal end for penetrating the anatomical cavity wall, said needle being movable relative to said cannula between an extended position and a retracted position proximally spaced from said extended position;
- a safety shield disposed between said cannula and said needle, said safety shield being movable relative to said needle between an extended safety shield rest position protecting said needle distal end when said needle is retracted and a safety shield retracted position exposing said needle distal end when said needle is extended;
- safety shield bias means for biasing said safety shield distally toward said safety shield rest position;
- retracting means for moving said needle from said needle extended position to said needle retracted position;
- means for manually moving said needle from said needle retracted position to said needle extended position;
- locking means for locking said needle in said needle extended position and preventing proximal movement of said needle during penetration of the anatomical cavity wall; and
- releasing means responsive to penetration of said safety needle instrument into the anatomical cavity for triggering release of said locking means to permit said retracting means to move said needle proximally to said needle retracted position.

12. A safety needle instrument as recited in claim 11 wherein said releasing means is responsive to distally-biased movement of said cannula upon penetrating into the anatomical cavity.

13. A safety needle instrument as recited in claim 11 wherein said releasing means is responsive to distally-biased movement of said safety shield upon penetrating into the anatomical cavity.

14. A safety needle instrument as recited in claim 11 wherein said releasing means is responsive to distally-biased movement of said cannula and said safety shield upon penetrating into the anatomical cavity.

15. A safety needle instrument as recited in claim 11 wherein said needle distal end extends distally from a junction where a transverse dimension of said needle changes and wherein said safety shield distal end is aligned with said junction when said safety shield is in said rest position and said needle is in said locked needle extended position.

16. A safety needle instrument as recited in claim 11 wherein said needle distal end extends distally from a junction where a transverse dimension of said needle changes and wherein said safety shield distal end is located proximally of said junction when said safety shield is in said rest position and said needle is in said locked needle extended position.

17. A safety needle instrument as recited in claim 11 wherein said needle distal end extends distally from a junction where a transverse dimension of said needle changes and wherein said safety shield distal end is located distally of said junction when said safety shield is in said rest position and said needle is in said locked needle extended position.

18. A safety needle instrument as recited in claim 11 wherein said needle distal end extends distally from a junction where a transverse dimension of said needle changes and wherein said cannula distal end is aligned with said junction when said cannula is in said rest position and said needle is in said locked needle extended position.

19. A safety needle instrument as recited in claim 11 wherein said needle distal end extends distally from a junction where a transverse dimension of said needle changes and wherein said cannula distal end is located proximally of said junction when said cannula is in said rest position and said needle is in said locked needle extended position.

20. A safety needle instrument as recited in claim 11 wherein said needle distal end extends distally from a junction where a transverse dimension of said needle changes and wherein said cannula distal end is located distally of said junction when said cannula is in said rest position and said needle is in said locked needle extended position.

21. A safety needle instrument for establishing a portal in the wall of an anatomical cavity comprising

- a housing;
- an elongate cannula having a proximal end mounted by said housing and a distal end for introduction in the anatomical cavity, said cannula being movable relative to said housing between an extended rest position and a proximally spaced retracted position;
- cannula bias means for biasing said cannula distally toward said cannula rest position;
- a needle disposed within said cannula and having a distal end for penetrating the anatomical cavity wall, said needle being movable relative to said cannula between an extended position and a retracted position proximally spaced from said extended position;
- a safety shield disposed between said cannula and said needle, said safety shield being movable relative to said needle between an extended safety shield rest position protecting said needle distal end when said needle is retracted and a safety shield retracted position exposing said needle distal end when said needle is extended;
- safety shield bias means for biasing said safety shield distally toward said safety shield rest position;
- retracting means for moving said needle from said needle extended position to said needle retracted position;
- means for manually moving said needle from said needle retracted position to said needle extended position;
- locking means for locking said needle in said needle extended position while permitting a predetermined amount of proximal movement of said needle during penetration of the anatomical cavity wall;

needle bias means for biasing said needle distally in said locked needle extended position to permit said needle to move proximally during penetration of the anatomical cavity wall and distally upon introduction into the anatomical cavity; and releasing means responsive to penetration of said safety needle instrument into the anatomical cavity for triggering release of said locking means to permit said retracting means to move said needle proximally to said needle retracted position.

22. A safety needle instrument as recited in claim 21 wherein said releasing means is responsive to distally-biased movement of said needle upon penetrating into the anatomical cavity.

23. A safety needle instrument as recited in claim 21 wherein said releasing means is responsive to distally-biased movement of said safety shield upon penetrating into the anatomical cavity.

24. A safety needle instrument as recited in claim 21 wherein said releasing means is responsive to distally-biased movement of said cannula upon penetrating into the anatomical cavity.

25. A safety needle instrument as recited in claim 21 wherein said releasing means is responsive to distally-biased movement of said needle and said safety shield upon penetrating into the anatomical cavity.

26. A safety needle instrument as recited in claim 21 wherein said releasing means is responsive to distally-biased movement of said needle and said cannula upon penetrating into the anatomical cavity.

27. A safety needle instrument as recited in claim 21 wherein said releasing means is responsive to distally-biased movement of said safety shield and cannula upon penetrating into the anatomical cavity.

28. A safety needle instrument as recited in claim 21 wherein said releasing means is responsive to distally-biased movement of said needle, safety shield and cannula upon penetrating into the anatomical cavity.

29. A safety needle instrument as recited in claim 21 wherein said needle distal end extends distally from a junction where a transverse dimension of said needle changes and wherein said safety shield distal end is aligned with said junction when said safety shield is in said rest position and said needle is in said locked needle extended position.

30. A safety needle instrument as recited in claim 21 wherein said needle distal end extends distally from a junction where a transverse dimension of said needle changes and wherein said safety shield distal end is located proximally of said junction when said safety shield is in said rest position and said needle is in said locked needle extended position.

31. A safety needle instrument as recited in claim 21 wherein said needle distal end extends distally from a junction where a transverse dimension of said needle changes and wherein said safety shield distal end is located distally of said junction when said safety shield is in said rest position and said needle is in said locked needle extended position.

32. A safety needle instrument as recited in claim 21 wherein said needle distal end extends distally from a junction where a transverse dimension of said needle changes and wherein said cannula distal end is aligned with said junction when said cannula is in said rest position and said needle is in said locked needle extended position.

33. A safety needle instrument as recited in claim 21 wherein said needle distal end extends distally from a junction where a transverse dimension of said needle changes and wherein said cannula distal end is located proximally of said junction when said cannula is in said rest position and said needle is in said locked needle extended position.

34. A safety needle instrument as recited in claim 21 wherein said needle distal end extends distally from a junction where a transverse dimension of said needle changes and wherein said cannula distal end is located distally of said junction when said cannula is in said rest position and said needle is in said locked needle extended position.

* * * * *